United States Patent
Matsuura

[11] Patent Number: 5,415,966
[45] Date of Patent: May 16, 1995

[54] IMAGE FORMING SYSTEM OF LOW OZONE GENERATION

[75] Inventor: Katsumi Matsuura, Hachioji, Japan
[73] Assignee: Konica Corporation, Japan
[21] Appl. No.: 149,631
[22] Filed: Nov. 9, 1993
[30] Foreign Application Priority Data
Nov. 18, 1992 [JP] Japan .................. 4-308872
[51] Int. Cl.[6] ........................... G03G 13/14
[52] U.S. Cl. ................... 430/126; 355/274
[58] Field of Search ............ 430/59, 83, 73, 126; 355/274

[56] References Cited

U.S. PATENT DOCUMENTS

| | | | |
|---|---|---|---|
| 5,024,912 | 6/1991 | Neishi et al. | 430/59 |
| 5,166,022 | 11/1992 | Suzuki et al. | 430/59 |
| 5,219,692 | 6/1993 | Shimada et al. | 430/59 |

FOREIGN PATENT DOCUMENTS 174972  7/1986  Japan .................. 430/59

*Primary Examiner*—John Goodrow
*Attorney, Agent, or Firm*—Jordan B. Bierman; Bierman and Muserlian

[57] ABSTRACT

In an apparatus for forming a toner image, a photoreceptor includes a plurality of layers, wherein the uppermost layer is a charge-transferring layer containing a charge-transferring material represented by the following general formula (1) and the oxygen gas permeability coefficient per unit thickness of the charge-transferring layer is not higher than $1.0 \times 10^{-7}$ (cc/cm$^2$.S.cmHG):

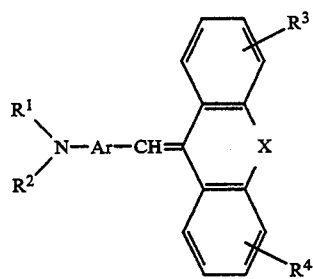

9 Claims, 7 Drawing Sheets

IMAGE FORMING SYSTEM OF LOW OZONE GENERATION

BACKGROUND OF THE INVENTION

The present invention relates to an image forming system provided with preventive means against ozone generation and capable of forming images stably without causing fatigue deterioration in the course of repeated image formation.

In the electrophotography based on the Carlson method, images are formed by the steps of electrifying the surface of a photoreceptor, forming latent images thereon through imagewise exposure, forming toner images through the development of said latent images, and transferring and fixing said toner images onto an image receiving material. After the transferring, the photoreceptor is subjected to processes of toner removal and charge neutralization to restore it to the original state, so that it is used repeatedly for a long period of time.

Accordingly, the photoreceptor for electrophotography needs a high durability which allows repetitive image formation over a long time, besides being high enough in electrophotographic properties such as electrification property, sensitivity, and residual potential property.

Meanwhile, there is given much attention in recent years to the organic photoreceptor using an organic photoconductor which is harmless, low in cost, high in processability and has a large degree of freedom in selecting a material suitable to use conditions of a photoreceptor. And the research and development is recently focussed on a function-separating type organic photoreceptor, in which the charge-generating function is allotted to a charge-generating material (hereinafter referred to as a CGM) and the charge-transferring function is allotted to a charge-transferring material (hereinafter referred to as a CTM).

Since a variety of hole-transferring p-type CTMs of high performance have been found, predominant function-separating type organic photoconductors in recent years are those having a CGM-containing charge-generating layer (hereinafter referred to as a CGL) which constitutes the lower layer and a CTM-containing charge-transferring layer (hereinafter referred to as a CTL) which constitutes the upper layer.

In the research and development of such organic photoreceptors, however, ozone generated by an electrifying or transferring corona discharger causes undesired problems, because it damages a CTM, particularly a CTM having high electrophotographic characteristics, to deteriorate the photoreceptive layer and, moreover, it is harmful to the human body. This necessitates the use of adequate preventive means against ozone generation.

As CTMs for the above organic photoreceptor, there are known styryl compounds, hydrazone compounds, pyrazoline compounds and triazole compounds as disclosed, for example, in Japanese Pat. O.P.I. Pub. No. 48869/1986. However, these are not necessarily adequate as a CTM for making a photoreceptor equivalent to a selenium photoreceptor. Under such conditions, Japanese Pat. O.P.I. Pub. No. 225660/1988, for example, discloses cycloheptanylidene derivatives and cycloheptenylidene derivatives of specific structure as CTMs capable of providing high sensitivities.

However, the CTMs comprising those cycloheptanylidene derivatives or cycloheptenylidene derivatives of specific structure are very low in resistance to ozone generated by corona discharge; therefore, a photoreceptor having a surface CTL containing such a CTM is affected by the ozone in the course of repetitive image formation, bringing about a considerable deterioration in electrophotographic properties.

For example, the following compound, one of the typical CTMs according to the present invention, showed a considerable deterioration when exposed to ozone, in an ozone resistance test conducted by the present inventors.

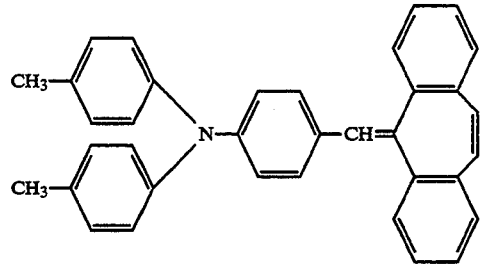

In the above ozone resistance test, the CTM was exposed to an atmosphere comprising 100 ppm ozone for 60 minutes by repeating a 10-minute exposure six times, and then its structural deterioration was determined from the change in peak value of absorption spectrum measured with a light resistance testing fluorescent lamp having a wavelength distribution shown in FIG. 6. The results are shown in FIG. 7, in which the intensities of absorption spectra after respective 10-minute exposures are given in percentages to the peak value of unexposed CTM which is set at 100. It is understood from FIG. 7 that the relative intensity of absorption spectrum lowers to about ½ or less when the CTM is exposed for 30 minutes.

As is apparent from the above description, even if a CTM high in sensitivity and other electrophotographic properties is newly developed, a photoreceptor comprising such a CTM is affected by ozone and halved in performance in the course of repetitive image formation. This lessens the degree of freedom to select an appropriate CTM and thereby makes it difficult to prepare a photoreceptor having desired electrophotographic properties.

On the other hand, various approaches are used to minimize the ozone generation from the viewpoint of the image-forming system. And much attention is given to the contact method, which uses a bias-voltage-applied conductive roller for electrifying or transferring unlike the corona discharge method using a discharging wire. The contact method is effective in reducing the amount of ozone generated in the image-forming system. However, in the increasing demand for a photoreceptor with much longer durability, it is difficult to reach a satisfactory solution only by such reaction-kinetics-based counter-measures against generation and influences of ozone in the image-forming system.

As the results of studies, the present inventors have found that high image qualities cannot be stably obtained in repetitive image formation unless the ozone concentration in the system is controlled within a certain range and, in conjunction with such control, the property of a photoreceptive layer is improved, when a photoreceptor used in the image forming system has a surface layer formed of a CTM which is susceptible to ozone deterioration, though high in electrophotographic properties, especially in sensitivity.

SUMMARY OF THE INVENTION

Accordingly, the object of the present invention is to provide an image forming system which uses a photoreceptor having high electrophotographic properties, particularly a high sensitivity, and is less in fatigue deterioration and capable of stably providing high image qualities in repetitive image formation over a long period of time.

The above object is attained by an image forming system comprising the following constituents:

a photoreceptor in which the uppermost layer is a CTL containing a CTM represented by the following formula (1) and the oxygen gas permeability coefficient per unit thickness of said CTL is not more than $1.0 \times 10^{-7}$ (ml/cm$^2$.S.cmHg), an electrifying means provided above the photoreceptor and having a capability of controlling ozone generation, a latent image forming means provided above the photoreceptor, a means to form toner images by developing latent images, a means to transfer toner images to an image receiving material, and a means to clean up the photoreceptor after transferring.

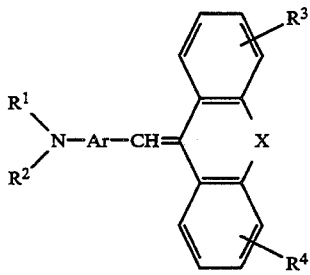

DETAILED DESCRIPTION OF THE PREFERRED EMBODIMENT

Figure 1:
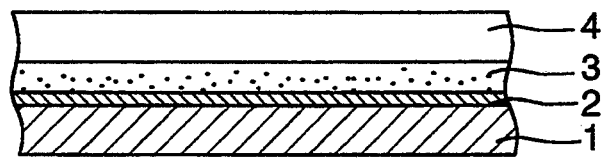
FIG. 1 is a cross sectional view of the layer configuration of the photoreceptor.

As shown in FIG. 1, the photoreceptor of the invention has the structure in which intermediate layer 2 is formed on conductive support 1, and CGL 3 and CTL 4 are formed on intermediate later 2 in this order. That is, with the object of preventing charge injection from conductive support 1 and enhancing adhesion to CGL 3, intermediate layer 2 is formed on the support in thicknesses of 0.01 to 2 μm by dip coating or spray coating of an organic high-molecular compound such as alkylated nylon, alkoxylated nylon, vinyl chloride-vinyl acetate copolymer, vinyl chloride-vinyl acetate-maleic anhydride copolymer, polyvinyl alcohol, ethyl cellulose, carboxymethyl cellulose, casein or starch, or by vacuum deposition or sputtering of aluminium oxide or the like.

Next, CGL 3 containing 5 to 500 parts by weight, preferably 20 to 300 parts by weight of CGM and, when necessary, 10 to 200 parts by weight of CTM per 100 parts by weight of binder resin is formed on intermediate layer 2 in thicknesses of 0.05 to 10 μm.

Subsequently, CTL 4 containing 20 to 200 parts by weight, preferably 30 to 100 parts by weight of CTM per 100 parts by weight of binder resin is formed on CGL 3 in thicknesses of 5 to 50 μm to obtain a photoreceptor.

The CGM contained in the CGL, though not particularly limited, includes the following compounds:

(1) Azo pigments such as monoazo pigments, polyazo pigments, metallic complex azo pigments, pyrazolone azo pigments, stilbene azo pigments and thiazole azo pigments (2) Perylene pigments such as perylenic anhydride and perylenimide (3) Anthraquinone pigments and polycyclic quinone pigments such as anthraquinone derivatives, anthanthrone derivatives, dibenzopyrene quinone derivatives, pyranethrone derivatives and isoviolanthrone derivatives (4) Indigoid pigments such as indigo derivatives and thioindigo derivatives (5) Phthalocyanine pigments such as metallic phthalocyanines and non-metallic phthalocyanine.

(6) Carbonium pigments such as diphenylmethane pigments, triphenylmethane pigments, xanthene pigments and acridine pigments (7) Quinoneimine pigments such as azine pigments, oxazine pigments and thiazine pigments (8) Methine pigments such as cyanine pigments and azomethine pigments (9) Quinoline pigments

(10) Nitro pigments

(11) Nitrone pigments

(12) Benzoquinone pigments and naphthoquinone pigments

(13) Naphthalimide pigments

(14) Perynone pigments such as bisbenzimidazole derivatives

Preferred pigments among these are azo pigments, perylene pigments, polycyclic quinone pigments and phthalocyanine pigments which can give high sensitivities to a photoreceptor.

As the CTM contained in the above CTL or CGL, the compound represented by the foregoing formula (1) is used, and thereby a photoreceptor of high sensitivity, long durability and high reliability can be obtained.

As the CTM having the structure of formula (1), cycloheptanylidene derivatives of the following formula (A) and cycloheptenylidene of the following formula (B) are preferred.

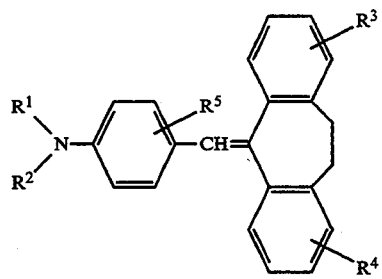
formula (A)
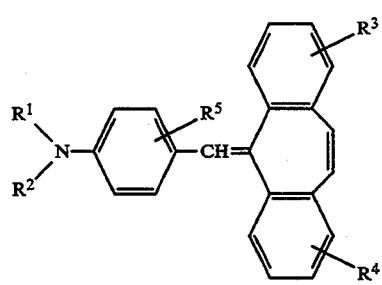
formula (B)
In the formulas, R1, R2, R3 and R4 are the same as those in formula (1), R5 represents a hydrogen or halogen atom, a nitro, alkyl or alkoxy group.
Typical examples of the CTM having the structure of formula (A) are as follows:
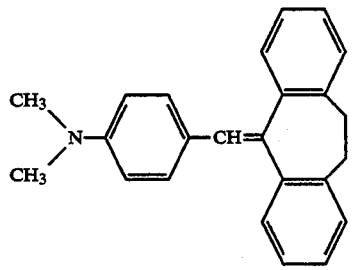
(1)-1
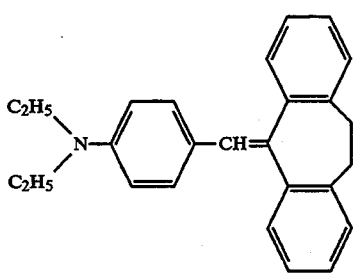
(1)-2
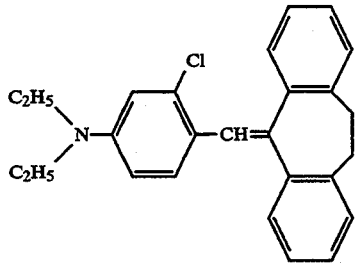
(1)-3
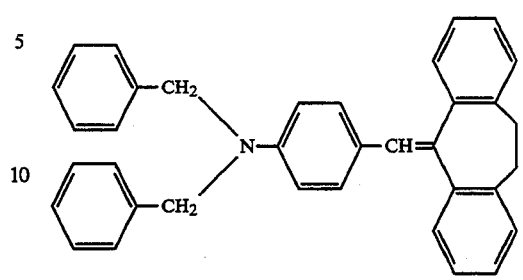
(1)-4
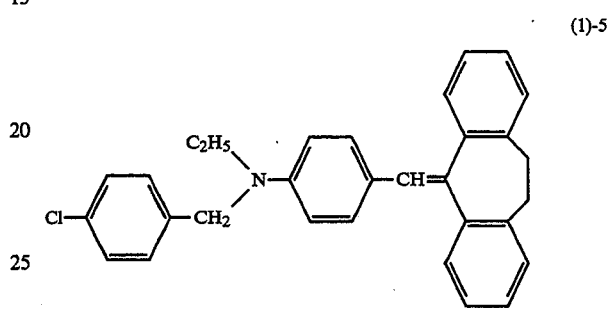
(1)-5
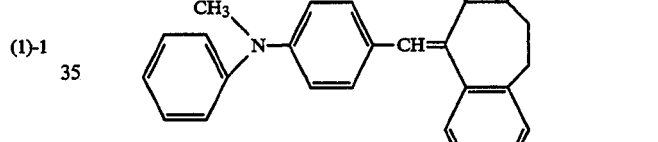
(1)-6
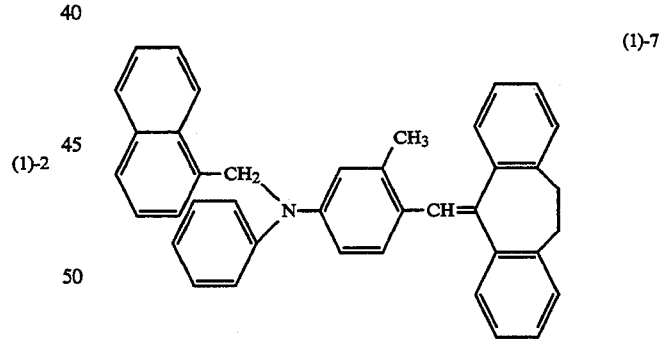
(1)-7
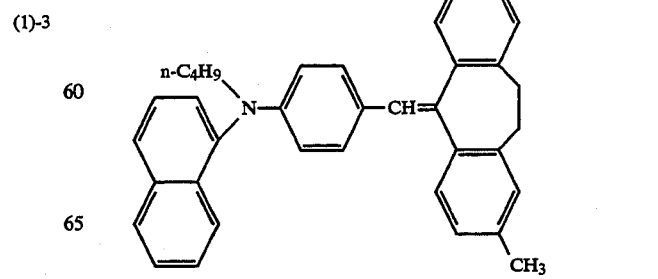
(1)-8

-continued
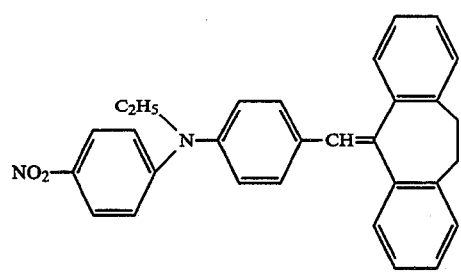
(1)-9
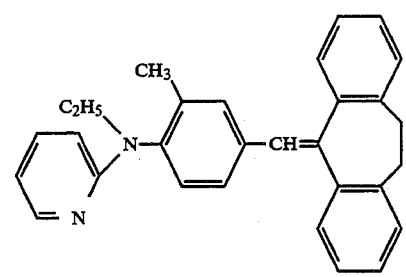
(1)-10
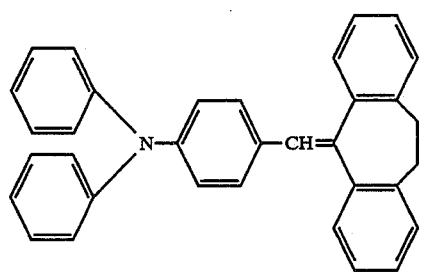
(1)-11
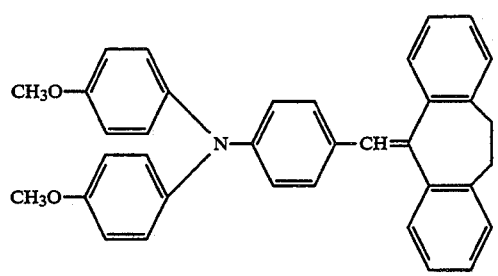
(1)-12
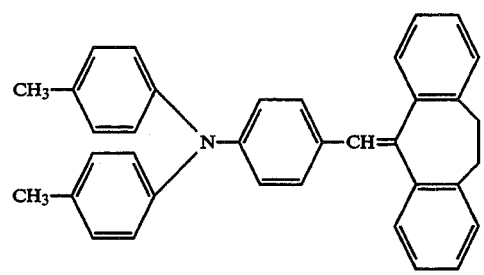
(1)-13
-continued
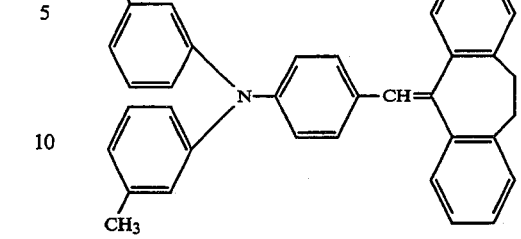
(1)-14
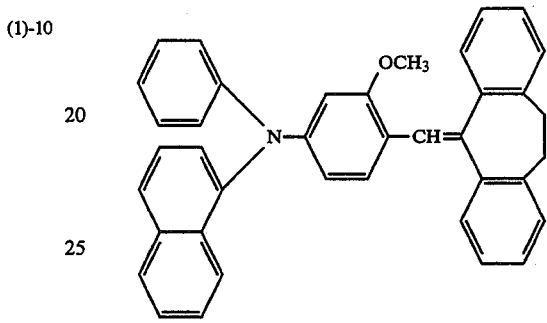
(1)-15
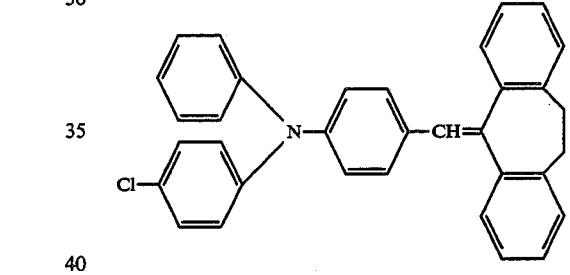
(1)-16
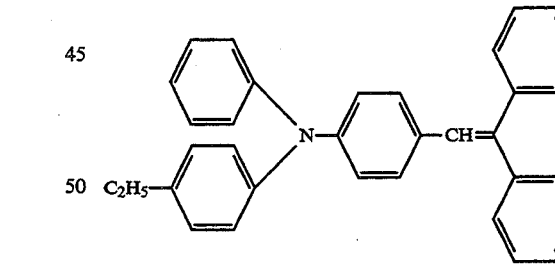
(1)-17
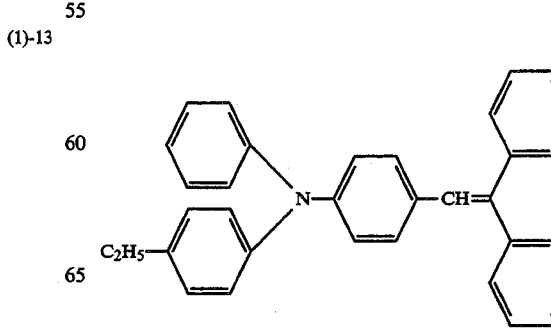
(1)-18

-continued
(1)-19
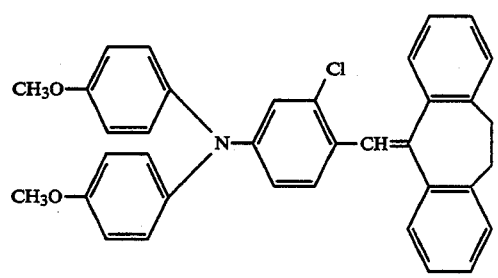
(1)-20
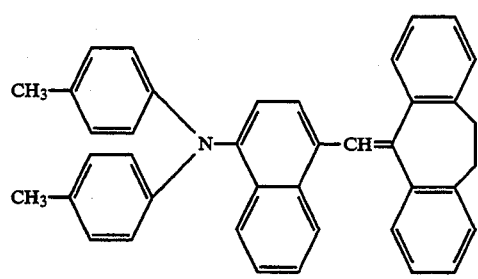
(1)-21
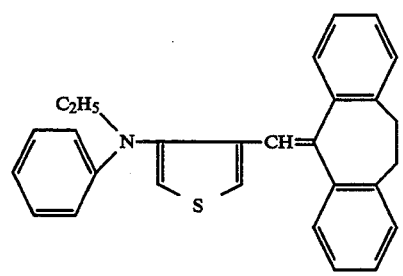
(1)-22
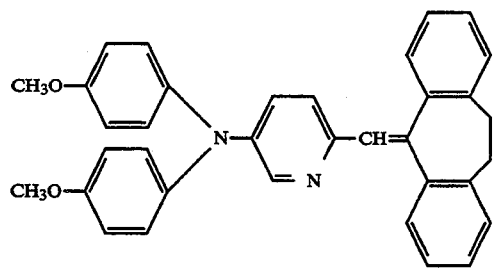
(1)-23
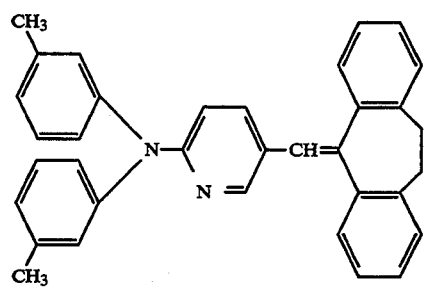
-continued
(1)-24
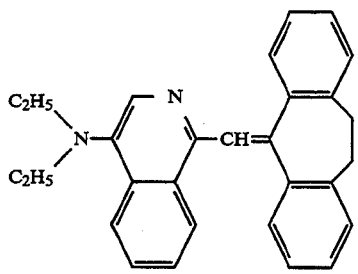
(1)-25
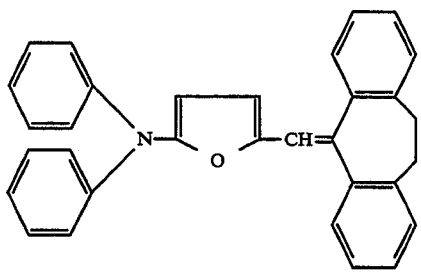
Typical examples of the CTM having the structure of formula (B) are shown below:
(2)-1
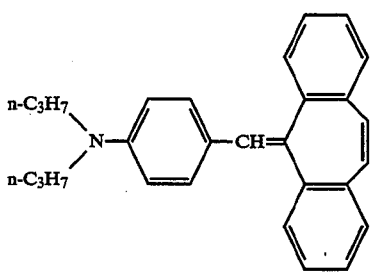
(2)-2
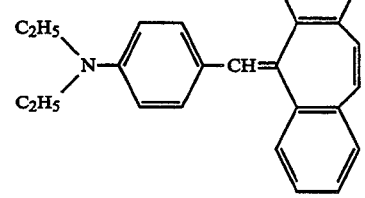
(2)-3
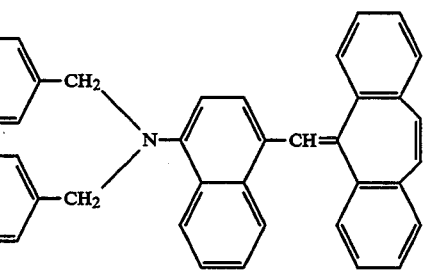

-continued
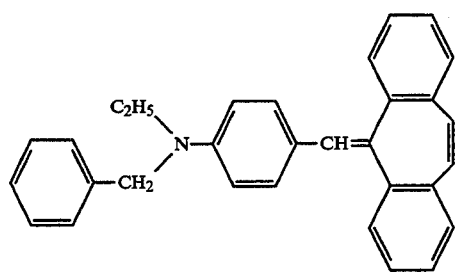
(2)-4
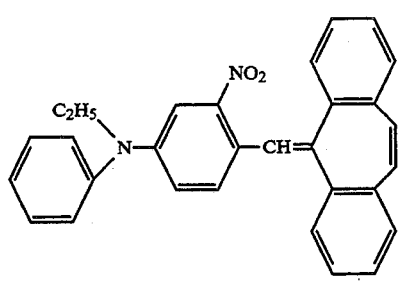
(2)-5
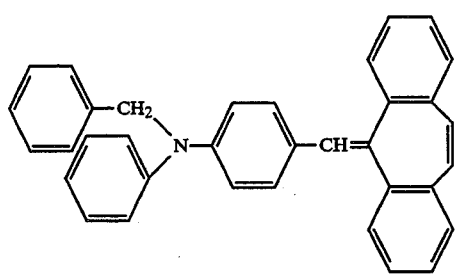
(2)-6
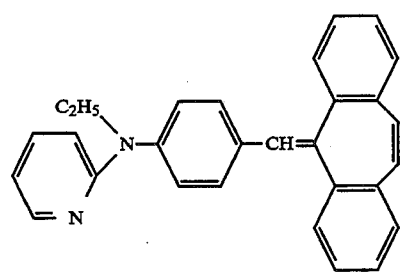
(2)-7
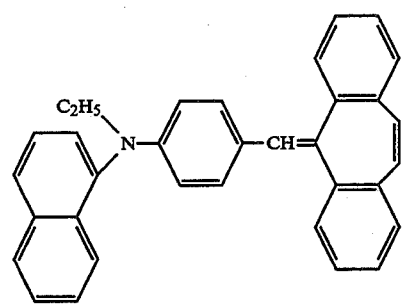
(2)-8
-continued
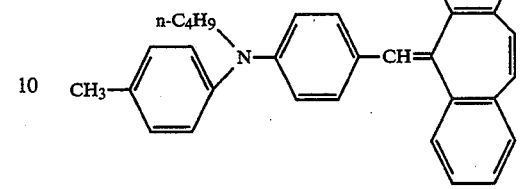
(2)-9
(2)-10
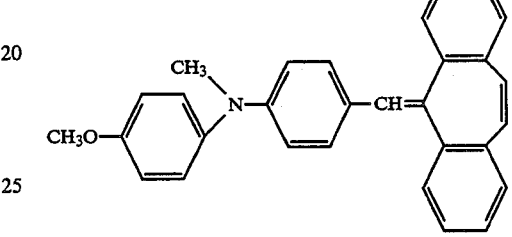
(2)-11
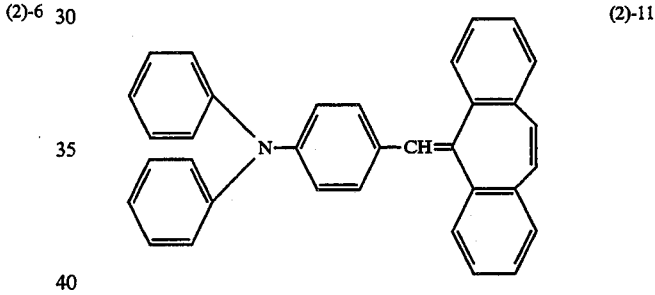
(2)-12
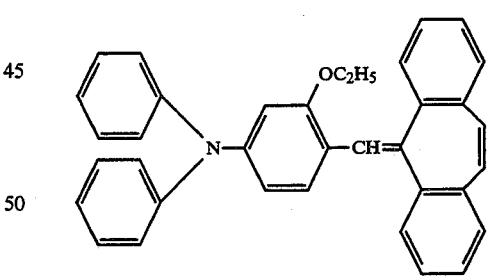
(2)-13
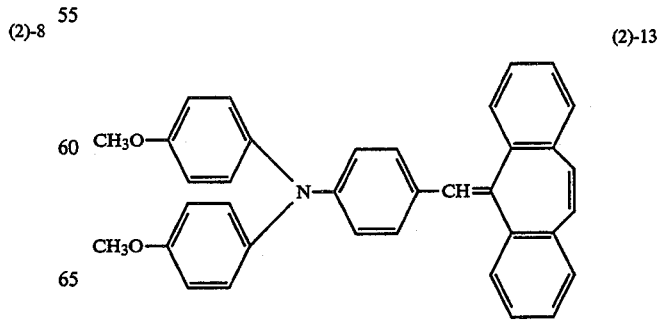

-continued
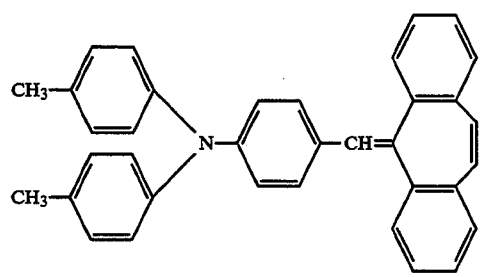
(2)-14
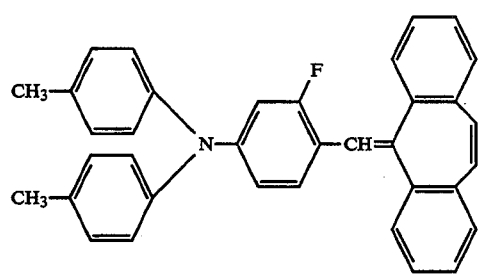
(2)-15
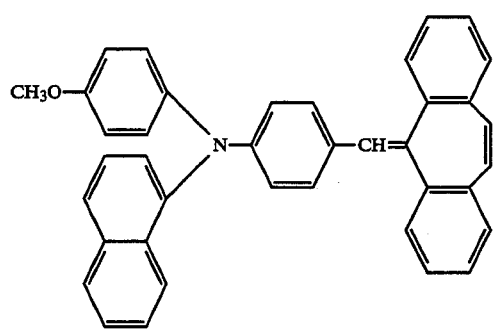
(2)-16
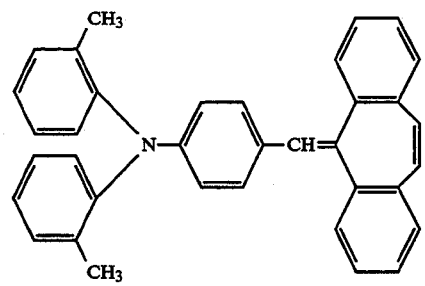
(2)-17
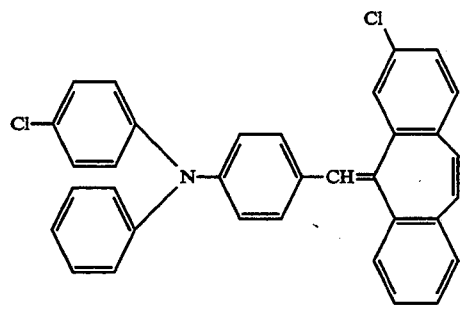
(2)-18
-continued
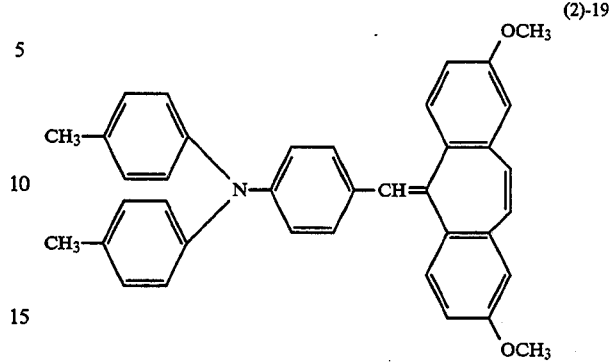
(2)-19
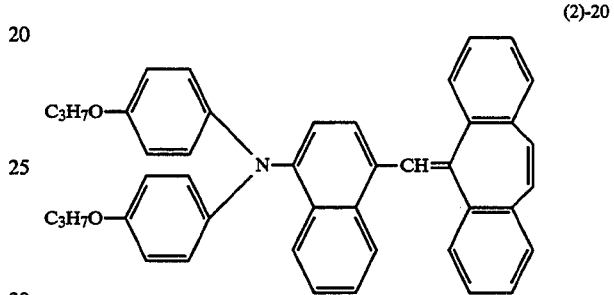
(2)-20
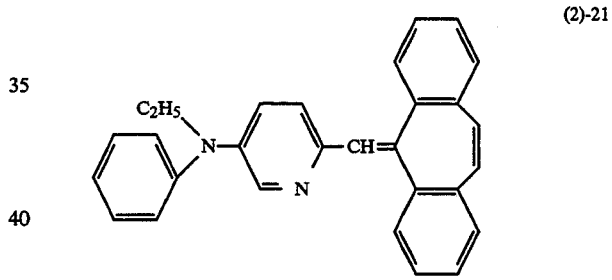
(2)-21
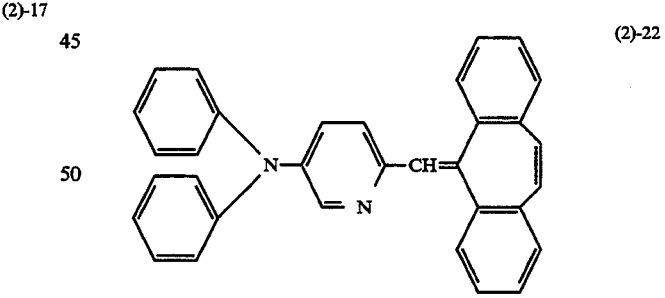
(2)-22
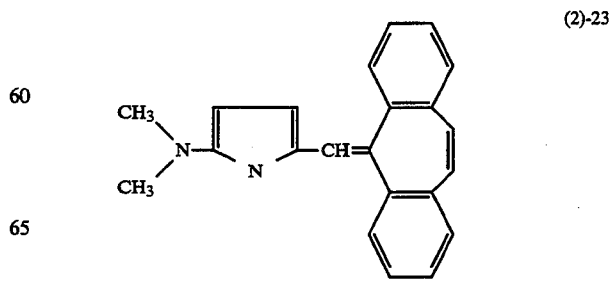
(2)-23

-continued (2)-24
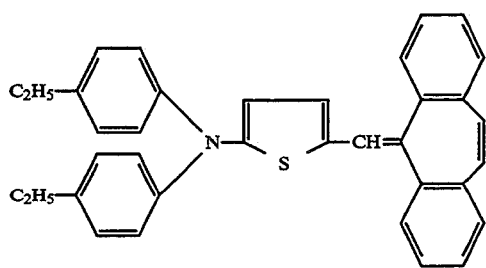

(2)-25
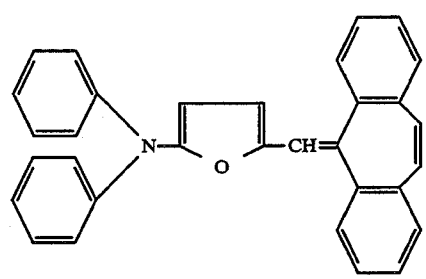

(2)-26
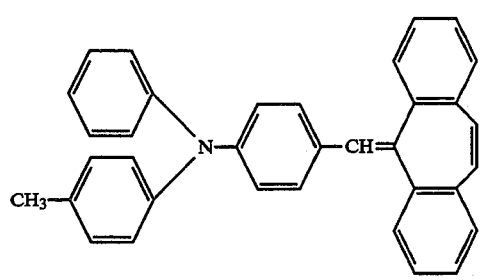

(2)-27
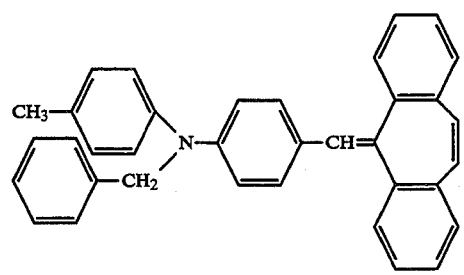

(2)-28
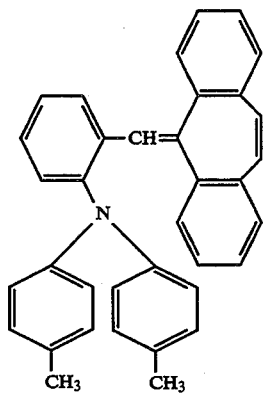

Any binder resin for electrophotographic application can be used as a binder in the above CGL and CTL. Suitable examples include insulating resins such as poly-addition resins and polycondensation resins including polyethylenes, polypropylenes, methacrylic resins, vinyl chloride resins, vinyl acetate resins, vinyl butyral resins, vinyl formal resins, epoxy resins, polyurethane resins, polyester resins, alkyd resins, polycarbonate resins, and copolymer resins containing at least two of the repeating units of these resins including vinyl chloride-vinyl acetate copolymer resins, vinyl chloride-vinyl acetate-maleic anhydride copolymer resins, as well as polymeric organic semi-conductors such as poly-N-vinyl carbazoles.

The CTL which constitutes the surface layer of the photoreceptor according to the invention is required to be uniform, accurate, stout and less gas-permeable.

Binder resins suitable to form such a CTL include thermosetting resins such as thermoserring epoxy resins, melamine resins, phenolic resins, urethane resins, silicone resins, acrylic resins and ester resins.

In addition to the above resins, polymeric compounds having the following structural unit can also be favorably used for the purpose of minimizing the ozone permeability as disclosed in U.S. Pat. No. 4,304,899.

(3)-1
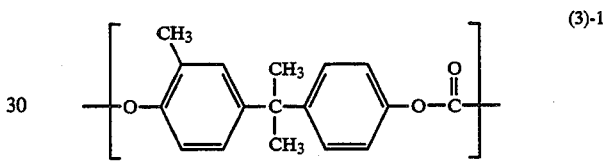

(3)-2
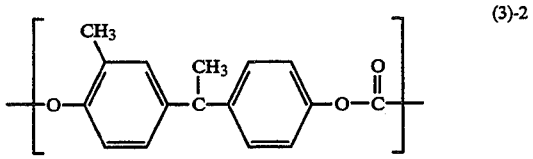

(3)-3
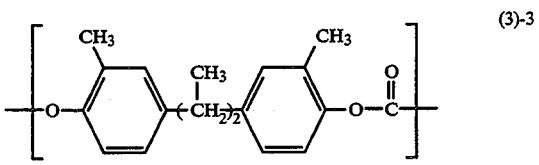

(3)-4
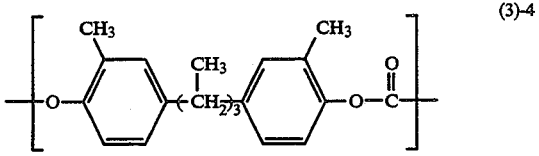

(3)-5
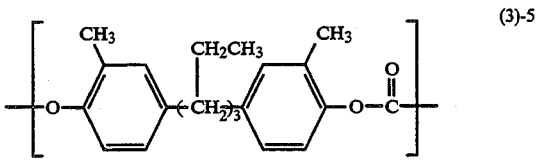

(3)-6
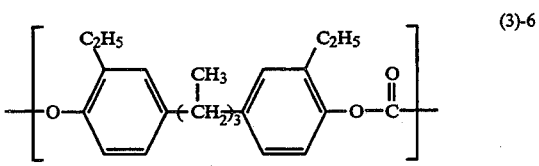

-continued

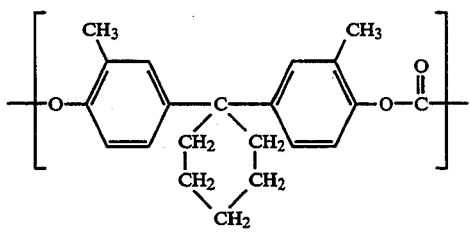
(3)-7

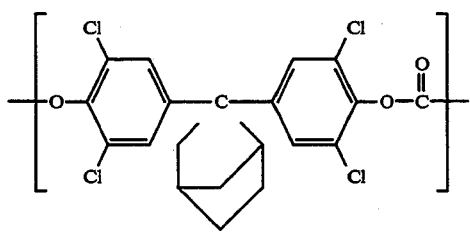
(3)-8

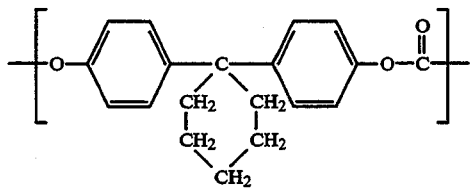
(3)-9

As dispersion media or solvents for the CGL and CTL of the invention, there can be used, for example, n-butylamine, diethylamine, ethylenediamine, isopropanolamine, monoethanolamine, triethanolamine, triethylenediamine, N,N-dimethylformamide, acetone, methyl ethyl ketone, cyclohexanone, benzene, toluene, xylene, chloroform, 1,2-dichloroethane, dichloromethane, tetrahydrofuran, dioxane, methanol, ethanol, isopropanol, ethyl acetate, butyl acetate and dimethyl sulfoxide.

Materials suitable for the conductive support are, for example, sheets of metals such as aluminium, nickel, copper, zinc, palladium, silver, indium, tin, platinum, gold, stainless steel and brass.

Further, there may be employed at least one electron-accepting material in the photoreceptive layer, for purposes of enhancing sensitivity and reducing residual potential and fatigue in repeated operation.

There may also be used silicone oils and fluorine-containing surfactants as surface property modifiers, and ammonium compounds as durability improvers.

In addition, ultraviolet absorbents may be used. Preferred are benzoic acid compounds, stilbene compounds and derivatives thereof as well as nitrogen-containing compounds such as triazole compounds, imidazole compounds, triazine compounds, coumarin compounds, oxaziazole compounds, thiazole compounds and derivatives thereof.

Antioxidants may be contained in the CTL and CGL in order to minimize the effect of ozone generated by discharge and prevent the rise in residual potential and the lowering in electrified potential during repeated operation.

Suitable antioxidants include hindered phenols, hindered amines, p-phenylenediamine, arylalkanes, hydroquinone, spirocoumarone, spiroindanone, derivatives of these compounds, organic sulfur compounds, and organic phosphorus compounds.

Typical examples thereof can be seen in Japanese Pat. O.P.I. Pub. Nos. 44667/1988, 50848/1988, 14153/1988, 50849/1988, 18355/1988, 58455/1988, 71857/1988, 71856/1988 and 146046/1988.

Next, explanation is made on the method for measuring an oxygen gas permeability coefficient per unit thickness of the CTL provided in the order of CGL and CTL on the conductive support according to the invention.

Figure 2:
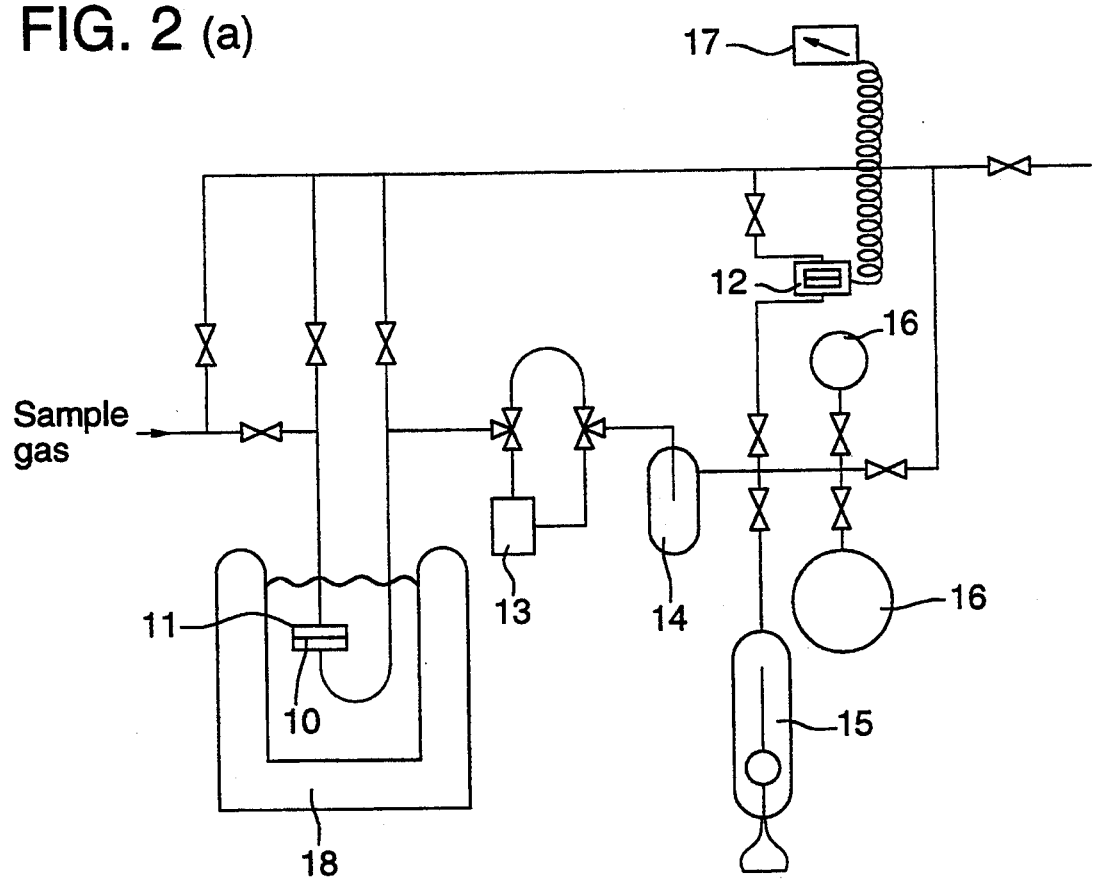
FIG. 2 (a) is a block diagram of the gas permeability coefficient measuring system, and FIG. 2 (b) is a graph showing the relationship between elapse of time t and pressure $P_b$ on low pressure side.
Figure 2:
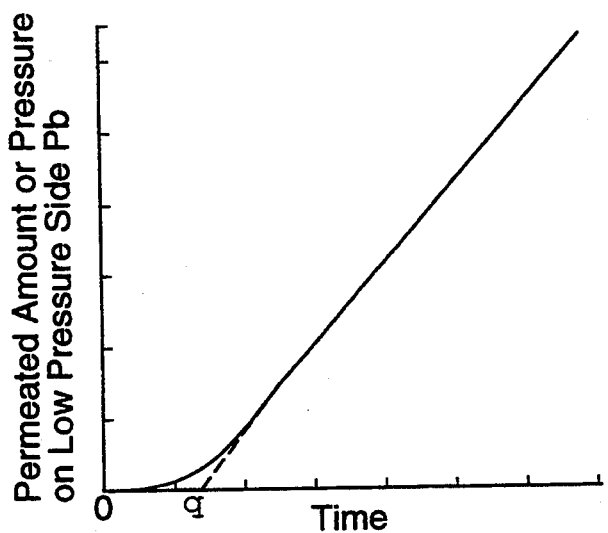

FIG. 2 (a) is a schematic diagram showing a measuring mechanism by means of a typical measuring system.

In the diagram, cell 11 holding sample 10 is set in thermostatic chamber 18, and oxygen gas for measuring a gas (oxygen gas) permeability coefficient is introduced into the high pressure side of cell 11. The oxygen gas on the high pressure side permeates through sample 10 to move to the low pressure side with the elapse of time, and thereby the pressure on the low pressure side changes.

The pressure change on the low pressure side is read and outputted as an electric signal by micro-differential pressure transducer 12, and the signal is amplified and recorded by recorder 17. In the diagram, 13 represents a low pressure side diffusion pump, 14 a trap, 15 a vacuum indicator, and 16 a reserve volume for sensitivity alteration.

FIG. 2 (b) shows an oxygen gas permeability curve recorded in an amplified form. The oxygen gas permeability coefficient P/1 per unit thickness of sample 10 can be determined by introducing the slope of the linear portion $\Delta P_b/\Delta t$ read from the above curve into the following equation:

$$P/1 = \frac{\Delta P_b}{\Delta t} \cdot \frac{V}{A} \cdot \frac{1}{P_0} \cdot \frac{T_0}{T} \cdot \frac{1}{(P_a - P_b)}$$

where,
P: gas permeability coefficient (ml/cm$^2$.S.cmHg) (S=sec)
V: volume of low pressure side (ml)
A: permeation area (cm$^2$)
1: sample thickness (cm)
$P_0$: standard pressure (1 atm=76 cmHg)
$P_a$: pressure of high pressure side (cmHg)
$P_b$: pressure of low pressure side (cmHg)
$T_0$: standard temperature (273° K.)
T: measuring temperature (K)
$\Delta P_b/\Delta t$: rate of pressure increase at a steady state on low pressure side, or slope of linear portion in a permeation curve (cmHg/s)

As a matter of course, this oxygen gas permeability coefficient varies with the kind, chemical structure and polymerization degree of binder. It also varies with the factors in the process to form the CTL, such as coating solvent, coating method, degree of drying, and concentrations of CTM and binder in a coating solution. Accordingly, the oxygen gas permeability coefficient changes when the state of the CTL varies with the above factors.

In the photoreceptor according to the invention, the oxygen gas permeability coefficient of the CTL, which forms the surface photoreceptive layer, is limited within a specific range as described above. As a result, penetration of oxygen gas, particularly penetration of ozone gas or the like into the CTL is prevented, and thereby deterioration of the CTM is limited to a small extent.

The penetration of harmful ozone gas or nitrogen oxide gases into the photoreceptive layer is thought to proceed in proportion to the above oxygen gas permeability coefficient. Therefore, as is apparent from examples of the invention described later, deterioration in electrophotographic properties due to repetitive operation can be substantially prevented by setting limits to the oxygen gas permeability coefficient of the CTL.

Since the structure of the image forming system of the invention is not particularly limited, the method for measuring the ozone concentration in the system is described below by referring to an image forming system having the ordinary structure.

Figure 3:
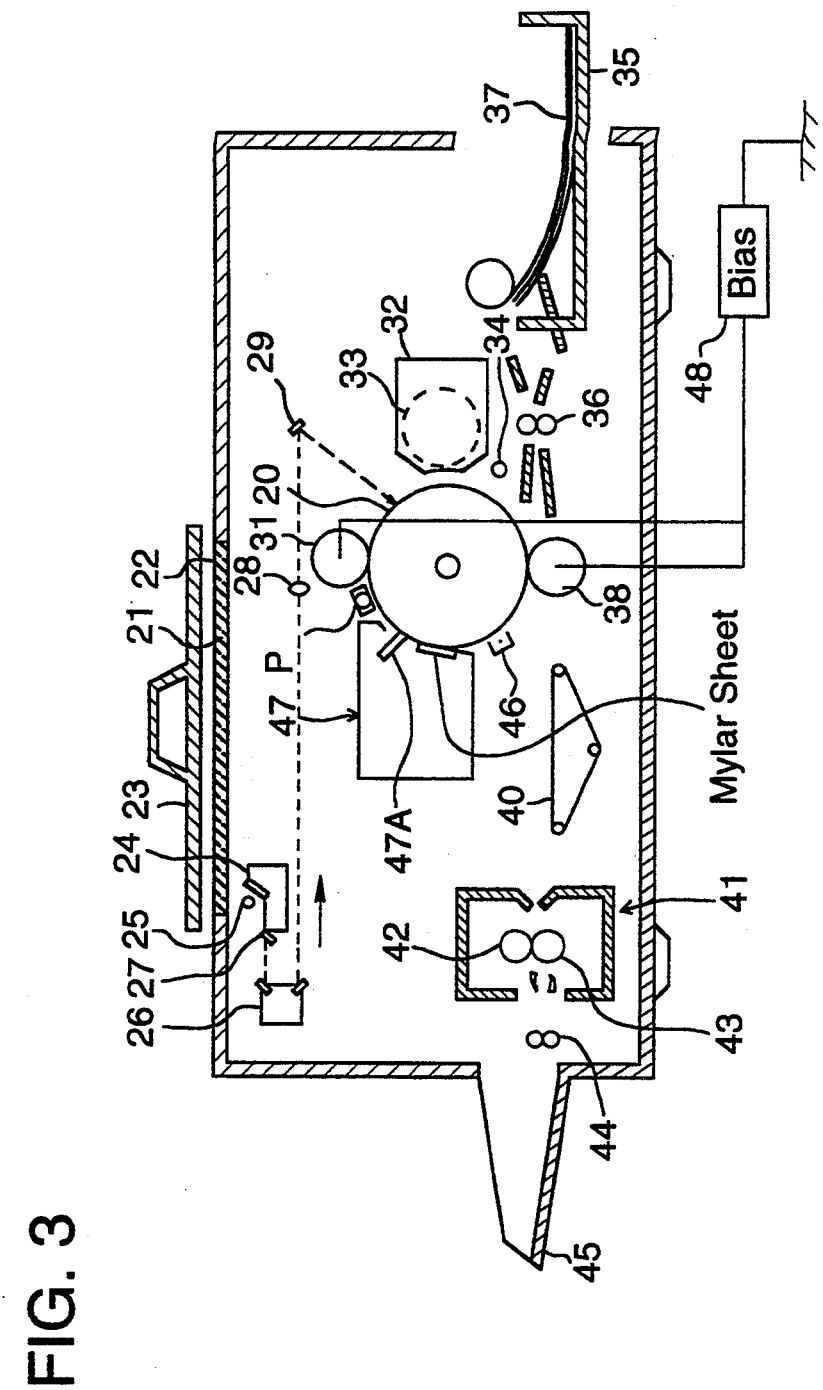
FIG. 3 is a schematic diagram of the image forming system used in the invention.

In FIG. 3 showing a schematic diagram of the image forming system, 21 represents a stand to hold an original, 22 an original and 23 a cover to hold an original down; the optical system for imagewise exposing comprises flood-lighting unit 24, exposing lamp 25, mirror unit 26, reflecting mirror 27, imaging lens 28 and reflecting mirror 29. An electrostatic latent image is formed by imagewise exposing through the above optical system on photoreceptor 20, which is uniformly electrified in advance by electrifying roller 31. This electrostatic latent image is developed into a toner image by a developer conveyed by sleeve 33 of developing unit 32.

The toner image is transferred by transferring roller 38 onto copying paper 37 conveyed by paper feeding roller 36 of paper feeding cassette 35. Then, the paper is separated from photoreceptor 20, sent to fixing unit 41 by conveyor belt 40 and subjected to fixing while it is being pressed between heating roller 42 and pressing roller 43. After transferring, photoreceptor 20 is destaticized by destaticizing lamp 34 and cleaned by blade 47A of cleaning unit 47 in preparation for the formation of a next image.

A DC bias voltage and, if necessary, an AC bias voltage are applied from electric source 49 to electrifying roller 31 and transferring roller 38 so as to electrify photoreceptor drum 20 and transfer a toner image onto copying paper 27. This bias voltage is usually a DC bias voltage ranging from 500 to 1000 V. When necessary, an AC bias voltage of 100 Hz to 10 KHz and 200 to 3500 V in $V_{p-p}$ may be applied additionally.

Figure 4:
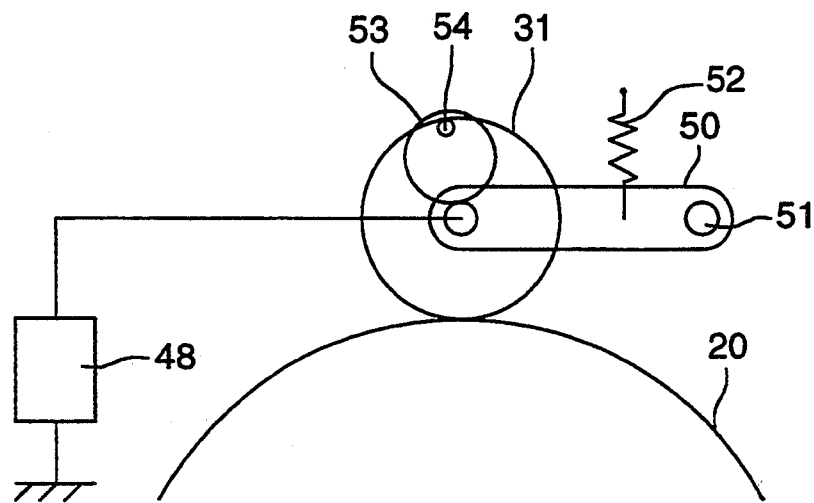
FIG. 4 (a) is a block diagram of the electrifying roller and transferring roller having a pressing and separating means, FIG. 4 (b) is a cross sectional view of the roller.
Figure 4:
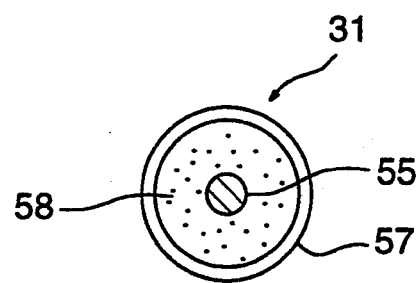

Preferably, electrifying roller 31 and transfer roller 38 each receiving the above bias voltage are separated, when out of operation, from photoreceptor drum 20 by the roller pressing and separating means shown in FIG. 4 (a), in order to prevent the wear and damage of the photoreceptor. In FIG. 4 (a), 50 shows a lever to keep roller 31 revolvable around shaft 51, and spring 52 keeps roller 31 apart from photoreceptor drum 20 during an unoperated time by pulling the roller upward; at the time of electrification (or transfer), roller 31 (or 38) is pressed against photoreceptor drum 20 by the rotation of eccentric cam 53 which overcomes the spring pressure of spring 52, so that electrification (or transfer) is carried out during a trailed movement (or a forced rotation) caused by photoreceptor drum 20.

This electrification process using an electrifying roller has a superiority over the conventional electrifying process using corona discharge in capability of controlling the generation of ozone.

In addition to the above, there are conceivable, as electrifying processes capable of controlling ozone generation, a variety of processes including that which uses an electrifying brush as disclosed in Japanese Pat. O.P.I. Pub. No. 91253/1981.

The pressure applied by roller 31 (or 38) to photoreceptor drum 20 is in the range of 10 to 100 g/cm, and the revolution speed of roller 31 (or 38) is 1 to 8 times the peripheral speed of photoreceptor drum 20.

As is apparent from the sectional view shown in FIG. 4 (b), roller 31 (or 38) has a rubber or foamed rubber layer, composed of a conductive chloroprene rubber, urethane rubber or silicone rubber, around metal stem 55 and, preferably, has a protective layer having thicknesses of 0.01 to 1 μm and composed of a releasing fluorocarbon resin or silicone resin as the outermost layer.

In measuring the ozone gas concentration in the image forming system, an Ozone Tester (product of Toyo Seiki Seisakusho Co., Ltd.) mounting an Ozone Monitor EG-2001R (product of Ebara Jitsugyo Co., Ltd.) is used.

Next, measurement of ozone gas concentration is described by taking the image forming system shown in FIG. 3 as an example. One end of a gas-sampling Teflon tube (sample gas intake) is fixed at position P in the image forming system, and the other end of the tube is fitted to the sample gas inlet of the foregoing ozone monitor. The concentration of the ozone gas from the image forming system is given in PPMs on the digital display of the monitor. The foregoing position P is set at a place which gives the highest ozone concentration in the vicinity of photoreceptor drum 20 and is located 5 m/m away from the photoreceptor drum. In general, the highest ozone concentration is frequently observed near the electrification electrode or OR transfer electrode.

In the invention, it is essential that the ozone gas concentration measured at position P with the foregoing ozone monitor mounted in the ozone tester be not more than 0.5 ppm. When the concentration exceeds 0.5 ppm, the repetitive properties of a high-sensitivity photoreceptor, particularly those of a photoreceptor using a CTM of the foregoing specific structure are deteriorated, bringing about considerable lowering in properties such as electrification potential, sensitivity and residual potential.

In general, the ozone concentration near the photoreceptor gradually increases with continuation of image formation, and measurement data with an electrophotographic apparatus on the market indicate that the ozone concentration reaches a saturated point when image formation is continuously repeated 5 to 10 times. In the invention, the maximum ozone concentration is defined to be the ozone concentration at which a saturated state is reached.

The invention is illustrated in detail with the following examples, but the embodiment of the invention is not limited to these examples.

EXAMPLE

Preparation of Photoreceptor and Electrostatic Property Measuring Samples

Preparation of Photoreceptor

An about 0.1-μm thick intermediate layer consisting of a vinyl chloride-vinyl acetate-maleic anhydride copolymer (Eslec MF-10 made by Sekisui Chemical Co., Ltd.) was provided on an 80-mm diameter aluminium cylinder. Then, 4 g of a bisazo dye of the following structure was ground for 24 hours in a ball mill, and 130 ml of 1,2-dichloroethane dissolving in it 2 g of a bisphenol A type polycarbonate (Panlite L-1250 made by Teijin Kasei Co., Ltd.) (hereinafter referred to as BPA) was added thereto, followed by a 24-hour dispersing. The resultant dispersion was dip-coated on the above intermediate layer and dried to obtain a CGL having a thickness of about 0.5 μm.

Subsequently, a solution containing 100 ml of 1,2-dichloroethane, 10 g of exemplified compound (1)-1 as a CTM, and 10 g of a polycarbonate having the structural unit of exemplified compound (3)-6 and a viscosity average molecular weight of 20,000 (hereinafter referred to as dimethyl BPZ) as a binder was dip-coated on the foregoing CGL, followed by drying at 80° C. for 1 hour to give a 20-Bin thick CTL. Thus, photoreceptor 1 was obtained.

nal thread 128 corresponding to threaded feed rod 116, threaded feed rod 116 penetrates through arm 118 with their threads engaging each other, and thereby arm 118 moves up and down, while supported by threaded feed rod 116, as threaded feed rod 116 rotates by means of motor 117.

Photoreceptor 2 was prepared by repeating the procedure of photoreceptor 1, except that exemplified compound (3)-9 was used in place of exemplified compound (3)-6 as the binder resin in the CTL.

Photoreceptor 3 was prepared likewise by repeating the procedure of photoreceptor 1, except that 7.5 g of dimethyl BPZ and 2.5 g of BPA were used in place of 10 g of dimethyl BPZ. Further, photoreceptors 4, 5 and

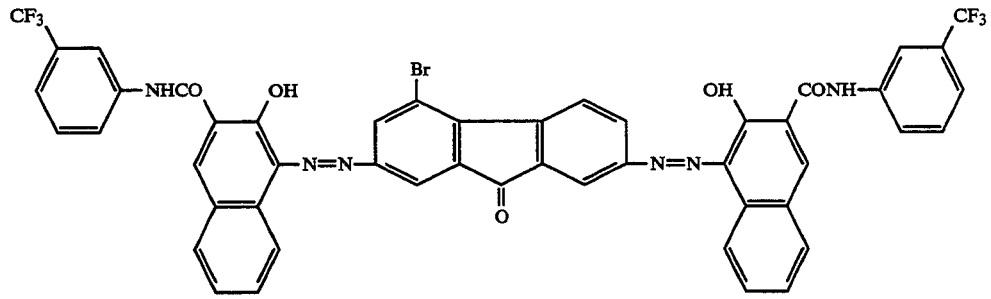

Figure 5:
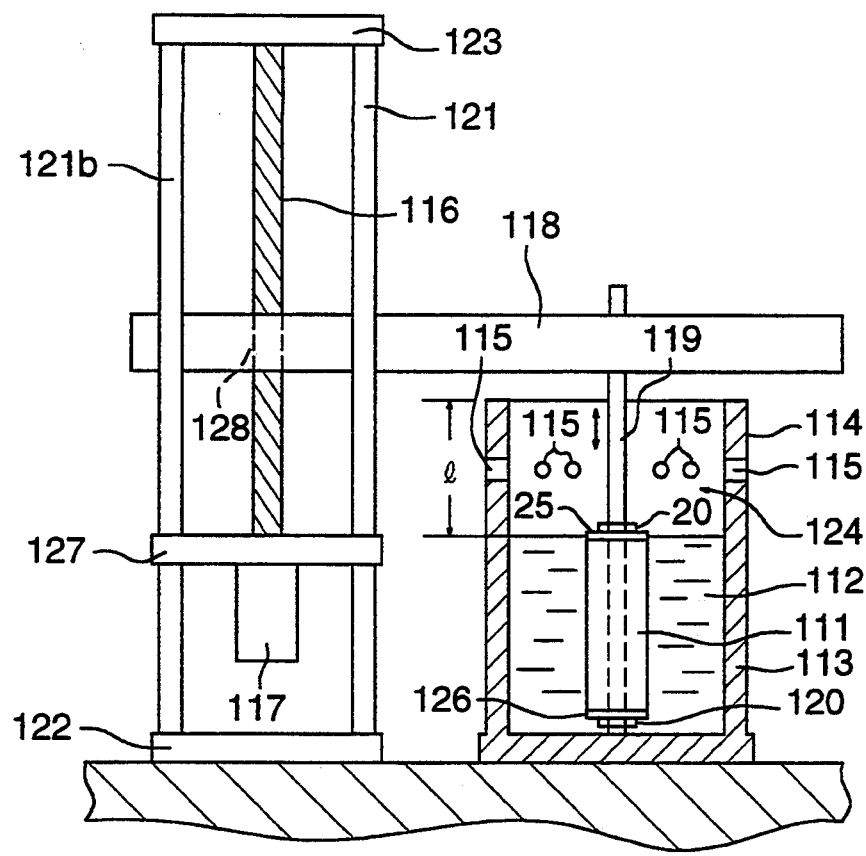
FIGS. 5 (a) and 5 (b) are cross sectional views of the dip coating system.
Figure 5:
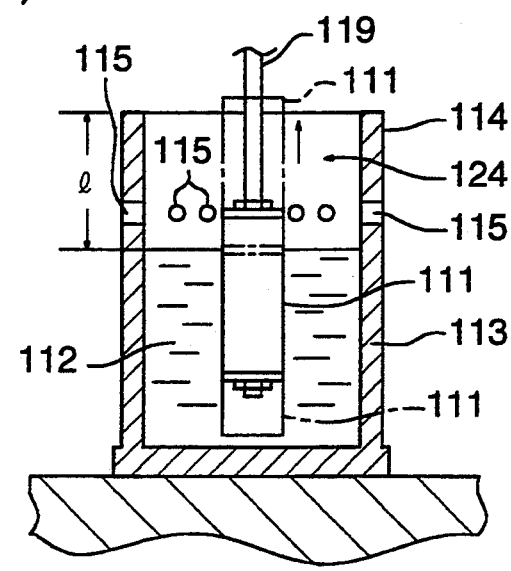
Figure 6:
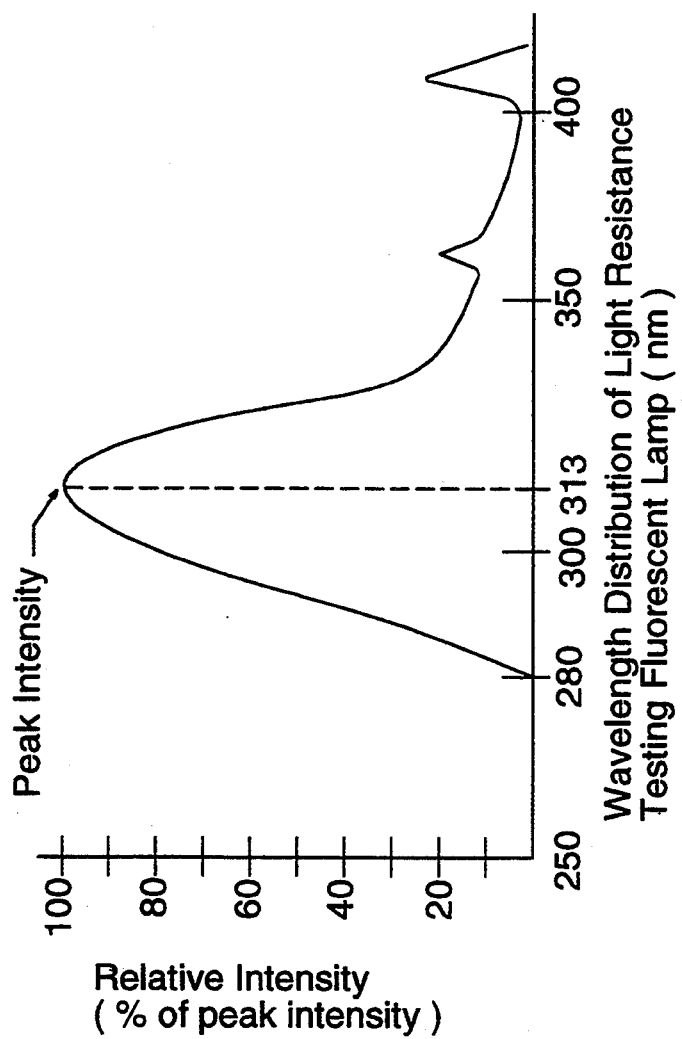
FIG. 6 is an emission spectrum of the light resistance testing fluorescent lamp.
Figure 7:
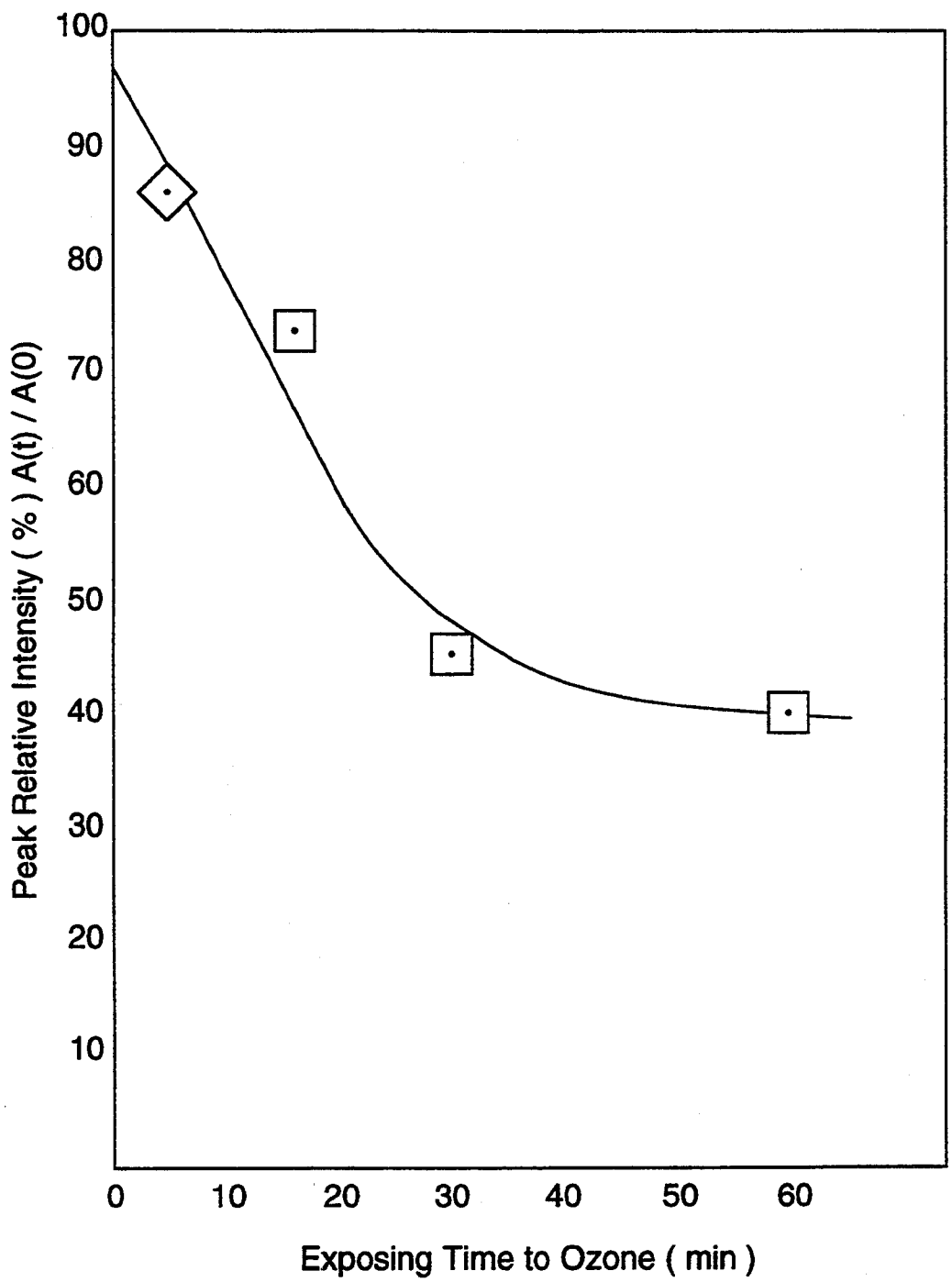
FIG. 7 is a curve showing change of CGM in peak value of absorption spectrum to the fluorescent lamp light caused by ozone deterioration.

The dip-coating was performed by use of the coating equipment shown in FIG. 5 (a) and (b). In FIG. 5, supporting rod 119, which penetrates through coating vessel 113 containing coating solution 112, holds aluminium cylinder 111 with the cylinder movable up and down. FIG. 5 (a) shows a state in which cylinder 111 is brought down to the low position and thereby fully immersed in coating solution 112. On vessel 113, there is jointedly provided cylinder-shaped covering member 114, which is about the same as vessel 113 in diameter and has perforations 115 in the side part to adjust the solvent vapor concentration distribution, and the inside of which constitutes drying zone 124.

That is, the dipping mechanism is designed, as shown in FIG. 5 (b), to pull out cylinder 111 in the immersed position of FIG. 5 (a) (shown by an alternate long and short dash line in FIG. 5 (b)) from coating solution 111, via an intermediate position shown by a solid line of FIG. 5 (b), by raising arm 118 which holds supporting rod 119 and, then, make it pass through drying zone 124 at a prescribed speed. To continue the dip-coating on the outside face of a cylinder, a new cylinder is fixed to supporting rod 119 in a position of being pulled out of drying zone 124 (or covering member 114), pulled down into coating solution 112, and then subjected to the above pulling out and drying processes.

Preferably, lids 125 and 126 are fixed with nuts 120 on both ends of cylinder 111 to cover the openings for preventing coating solution 112 from coming into cylinder 111. (The upper lid is not always necessary, the necessity for it depends upon the immersed depth of cylinder 111)

The mechanism of the vertical motion of arm 118 is as follows: Pillars 121a and 121b are vertically fixed on base 122, and the pillars' upper ends are fixed on upper base 123 which supports threaded feed rod 116 extending vertically. The lower end of threaded feed rod 116 penetrates through the center of fixing plate 127 fixed to pillars 121a and 121b, and is combined into one with the revolving shaft of motor 117 mounted on the lower side of fixing plate 127. Since arm 118 is provided with inter- 6 were prepared likewise, except that the binder resin for the CTL of photoreceptor 1 (10 g of dimethyl BPA) was replaced by (5.0 g of dimethyl BPZ and 5.0 g of BPA), (2.5 g of dimethyl BPZ and 7.5 g of APA) and (10 g of BPA) respectively, and that exemplified compound (2)-14 was used as the CTM.

Preparation of Electrostatic Property Measuring Samples

Photoreceptive plates E-1 to E-6 corresponding to the above photoreceptors 1 to 6 were prepared in the same manner as photoreceptor 1, except that PET bases laminated with aluminium foil were used in place of aluminium cylinders.

Then, four test samples having a size of about 40 min×40 mm were cut out of each of the 6 photoreceptive plates; that is, samples E-1-1 to E-1-4 were cut out of photoreceptive plate E-1, samples E-2-1 to E-2-4 out of photoreceptive plate E-2, samples E-3-1 to E-3-4 out of photoreceptive plate E-3, samples E-4-1 to E-4-4 out of photoreceptive plate E-4, samples E-5-1 to E-5-4 out of photoreceptive plate E-5, and samples E-6-1 to E-6-4 out of photoreceptive plate E-6. After classifying them into respective groups, the samples of the first group (E-1-1 to E-6-1) were put into a chamber of Ebara's Ozone Tester in which the foregoing Ozone Monitor EG-2001R was built in. Then, ozone gas was introduced into the chamber to a concentration of 0.1 ppm from the ozone generator of the ozone tester, and the samples were stored therein for 30 days at 25° C. to obtain the first group samples for the measurement with an electrometer.

During the storing, the temperature of the above ozone was shown on the monitor display as digital data, and the fluctuation in ozone concentration was automatically recorded over the whole period of 30 days.

Subsequently, samples for the measurement with an electrometer were prepared for the second group (E-1-2 to E-6-2), the third group (E-1-3 to E-6-3) and the fourth group (E-1-4 to E-6-4) in the same manner as the samples of the first group, except that the ozone concentrations were changed to 0.5 ppm, 0.6 ppm and 1.0 ppm, respectively.

Measurement of Electrostatic Properties

These 20 samples of 4 groups were subjected to measurement of electrostatic properties by turns on an Electrometer EPA-8100 (product of Kawaguchi Denki Seisakusho Co., Ltd.).

In the measurement, the surface potential VA obtained by electrifying the surface of the sample for 5 seconds at an electrification voltage of −6.0 KV was determined. Then, the exposure $E_{\frac{1}{2}}$ (lux.sec) necessary to attenuate the surface potential VA to half (half value exposure) under illumination of a tungsten lamp at an illumination intensity of 30 lux at the photoreceptor surface as well as the surface potential VR (residual potential) after exposing at an exposure of 30 lux.sec were determined. The values obtained are shown in Table 1.

bases. Obtained were 20-μm thick samples T-1 to T-6 for measuring oxygen gas permeability coefficients, which were CTLs corresponding to photoreceptors 1 to 6.

Measurement of Oxygen Gas Permeability Coefficients

Samples T-1 to T-6 were set by turns on cell 11 of the gas permeability coefficient measuring equipment shown in FIG. 2, and measurement was made using oxygen gas, during which the temperature of thermostatic chamber 18 was kept st 35° C.

The steps of the measurement are as follows: when a prescribed oxygen gas pressure $P_a$ (high pressure side) is applied to a sample, the oxygen gas on the high pressure side permeates to the low pressure side (gas pressure $P_b$) through the sample with the elapse of time. Thus, the gas pressure $P_b$ on the low pressure side changes.

The oxygen gas permeability coefficient per unit coating thickness is determined by plotting the change in oxygen gas pressure of low pressure side in relation to

TABLE 1

| | | Properties Photoattenuation of Potential in 30-Day Storage at Various Ozone Concentrations | | | | | | | | | | |
|---|---|---|---|---|---|---|---|---|---|---|---|---|
| | | 0.2 ppm | | | 0.5 ppm | | | 0.6 ppm | | | 1.0 ppm | | |
| Sample (E) No. | | $V_A$ | $E_{\frac{1}{2}}$ | $V_R$ | $V_A$ | $E_{\frac{1}{2}}$ | $V_R$ | $V_A$ | $E_{\frac{1}{2}}$ | $V_R$ | $V_A$ | $E_{\frac{1}{2}}$ | $V_R$ |
| Invention | E-1 (Photoreceptive Layer of Photoreceptor 1) | 720 | 1.1 | 10 | 720 | 1.2 | 15 | 720 | 1.5 | 30 | 720 | 2.3 | 55 |
| | E-2 (Photoreceptive Layer of Photoreceptor 2) | 720 | 1.1 | 10 | 720 | 1.2 | 15 | 720 | 1.7 | 35 | 720 | 2.7 | 60 |
| | E-3 (Photoreceptive Layer of Photoreceptor 3) | 720 | 1.0 | 5 | 720 | 1.1 | 10 | 720 | 1.6 | 35 | 720 | 2.5 | 60 |
| | E-4 (Photoreceptive Layer of Photoreceptor 4) | 720 | 1.1 | 10 | 720 | 1.2 | 15 | 720 | 1.6 | 35 | 720 | 2.5 | 60 |
| Comparison | E-5 (Photoreceptive Layer of Photoreceptor 5) | 720 | 1 5 | 30 | 720 | 1.7 | 40 | 720 | 2.0 | 45 | 720 | 3.0 | 70 |
| | E-6 (Photoreceptive Layer of Photoreceptor 6) | 720 | 1.6 | 35 | 720 | 1.8 | 45 | 720 | 2.2 | 50 | 720 | 3.5 | 75 |

Preparation of Samples for Measuring Oxygen Gas Permeability Coefficient (T)

Each of the CTL coating solutions of photoreceptors 1 to 6 was coated on a PET base fastened round an 80-mm diameter aluminium cylinder with the coating system of FIG. 5, followed by drying for 24 hours at 90° C. After cooling, the CTLs were peeled from the PET the elapse of time to prepare a permeability curve as shown in FIG. 2 (b), reading the slope of the linear portion $\Delta P_b/\Delta t$ in the curve, and introducing the reading of the slope into the foregoing equation for calculating a gas permeability coefficient. The results are shown in Table 2.

TABLE 2

| | | Properties | | |
|---|---|---|---|---|
| | | Components of Sample (T) | | Oxygen Gas Permeability Coefficient per Unit Coating Thickness |
| Sample (T) No. | | CTM | Binder Resin | (ml/cm² · S · cmHg) |
| Invention | T-1 (CTL of photoreceptor 1) | Exemplified compound (1)-1 | dimethyl BPZ 100% | $0.0757 \times 10^{-7}$ |
| | T-2 (CTL of photoreceptor 2) | Exemplified compound (1)-1 | Exemplified compound (3)-9 | $0.1673 \times 10^{-7}$ |
| | T-3 (CTL of photoreceptor 3) | Exemplified compound (1)-1 | dimethyl BPZ 75%, BPA 25% | $0.385 \times 10^{-7}$ |
| | T-4 (CTL of photoreceptor 4) | Exemplified compound (2)-14 | dimethyl BPZ 50%, BPA 50% | $0.975 \times 10^{-7}$ |
| Comparison | T-5 (CTL of photoreceptor 5) | Exemplified compound (2)-14 | dimethyl BPZ 25%, BPA 75% | $1.11 \times 10^{-7}$ |
| | T-6 (CTL of photoreceptor 6) | Exemplified compound (2)-14 | dimethyl BPA 100% | $1.41 \times 10^{-7}$ |

Image Forming Test

EXAMPLE 1

Using a modified Konica U-Bix 3035 mounting photoreceptor 1 and equipped with the electrifying roller and transferring roller illustrated in FIGS. 3 and 4 as the electrifier and transfer device, image formation was repeated 200,000 times in the atmosphere of 20° C. and 60% RH. Then, the image quality of copies in the initial stage and the final copy (the 200,000th copy) were evaluated. Ozone concentrations were measured at the initial and final stages of the image formation. The results are shown in Table 3.

In evaluating the image quality, a Macbeth RD918 was employed as a densitometer for measuring fog densities and maximum densities ($D_{max}$).

EXAMPLES 2, 3 AND 4

The procedure of Example 1 was repeated, except that photoreceptors 2, 3 and 4 were used in place of photoreceptor 1. The evaluation results of image quality and ozone concentration are shown in Table 3.

COMPARATIVE EXAMPLES 1 AND 2

The procedure of Example 1 was repeated, except that photoreceptors 5 and 6 were used in place of photoreceptor 1. The evaluation results of image quality and ozone concentration are shown in Table 3.

COMPARATIVE EXAMPLE 3

The procedure of Example 1 was repeated, except that a corona discharger was used in place of the electrifying roller and transferring roller. The evaluation results of image quality and ozone concentration are shown in Table 3.

As is apparent from the above descriptions, the image forming system of the invention makes it possible to use a photoreceptor having a large degree of freedom in selecting a charge transfer material of high electrophotographic characteristics, having high electrophotographic properties, particularly a high sensitivity, and causing less fatigue deterioration in a long repetitive operation; therefore, the system can stably provide high-quality images over a long period of time.

What is claimed is:

1. An apparatus for forming a toner image, said apparatus comprising;
    a photoreceptor including a plurality of layers, wherein an uppermost layer is a charge-transferring layer containing a charge-transferring material of Formula (1), an oxygen gas permeability coefficient per unit thickness of said charge-transferring layer being not greater than $1.0 \times 10^{-7}$ ($cc/cm^2 \cdot S \cdot cmHg$);
    a charger for providing said photoreceptor with an electric charge, said charger generating ozone in an amount whereby a maximum ozone concentration in said apparatus is not greater than 0.5 ppm;
    an exposing device for forming a latent image on said photoreceptor;
    a developing device for developing said latent image to form a toner image;
    a transferrer for transferring said toner image onto a recording sheet; and a cleaner for cleaning said photoreceptor after said toner image has been transferred:

TABLE 3

| Example No. Comp. Example No. | | Photo-receptor Tested | Electrification Transfer | Ozone Concentration Initial Stage | Ozone Concentration Final Stage | Image Quality Initial Stage | Image Quality Final Stage |
|---|---|---|---|---|---|---|---|
| Inventive Example | 1 | Photo-receptor 1 | electrifying roller H transferring roller H | 0.05 | 0.2 | no fogging, $D_{max}$ is more than 1.3, good image quality | no fogging, $D_{max}$ is more than 1.3, good image quality |
| | 2 | Photo-receptor 2 | electrifying roller H transferring roller H | 0.05 | 0.2 | no fogging, $D_{max}$ is more than 1.3, good image quality | no fogging, $D_{max}$ is more than 1.3, good image quality |
| | 3 | Photo-receptor 3 | electrifying roller H transferring roller H | 0.05 | 0.2 | no fogging, $D_{max}$ is more than 1.3, good image quality | no fogging, $D_{max}$ is more than 1.3, good image quality |
| | 4 | Photo-receptor 4 | electrifying roller H transferring roller H | 0.05 | 0.2 | no fogging, $D_{max}$ is more than 1.3, good image quality | no fogging, $D_{max}$ is more than 1.3, good image quality |
| Comparative | (1) | Photo-receptor 5 | electrifying roller H transferring roller H | 0.05 | 0.2 | no fogging, $D_{max}$ is more than 1.3, good image quality | fogging of 0.07, blurred image |
| | (2) | Photo-receptor 6 | electrifying roller H transferring roller H | 0.05 | 0.2 | no fogging, $D_{max}$ is more than 1.3, good image quality | fogging of 0.09, blurred image |
| | (3) | Photo-receptor 1 | corona discharge corona discharge | 0.7 | 1.3 | no fogging, $D_{max}$ is more than 1.3, good image quality | fogging of 0.12, $D_{max}$ is as low as 1.0, blurred image |

It is understood from Tables 1, 2 and 3 that the use of the above image forming system enables stable formation of high-quality images over a long time from the initial stage of the operation without lowering the image quality, because the image forming system uses a photoreceptor having a CTL which depresses permeation of gases such as oxygen, and the ozone concentration in the system is controlled to 0.5 ppm and below.

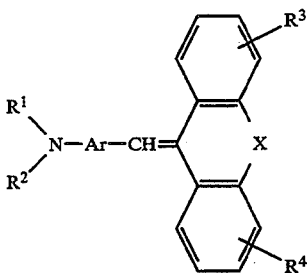

wherein X represents —$CH_2CH_2$— or —CH=CH—, $R^1$ and $R^2$ represent alkyl group, aralkyl group, aromatic ring group, or heterocycle group, $R^3$ and $R^4$ represent a hydrogen atom, alkyl group, alkoxy group, or a halogen atom, and Ar represents aromatic ring group or heterocycle group.

2. An apparatus for forming a toner image, said apparatus comprising;
- a photoreceptor comprising a plurality of layers, an uppermost layer being a charge-transferring layer containing a charge-transferring material, an oxygen gas permeability coefficient per unit thickness of said charge-transferring layer being not higher than $1.0 \times 10^{-7}$ (cc/cm$^2$.S.cmHg);
- a charger for providing said photoreceptor with an electric charge, said charger generating ozone whereby, a maximum concentration of ozone in said apparatus is not greater than 0.5 ppm;
- an exposing device for forming a latent image on said photoreceptor;
- a developing device for developing said latent image to form a toner image;
- a transferrer for transferring said toner image onto a recording member; and
- a cleaner for cleaning residual toner from said photoreceptor after said toner image has been transferred.

3. The apparatus of claim 1, wherein the charger is a roller type charger.

4. The apparatus of claim 3, wherein the charge-transferring layer contains dimethyl BPZ as a binder.

5. The apparatus of claim 3, wherein the charge-transferring layer contains BPZ as a binder.

6. A method of forming an image using an image forming apparatus comprising a photoreceptor, charger, latent image forming device, developer device, transferrer and cleaner, said charger generating ozone in an amount whereby a maximum ozone concentration in said apparatus is not higher than 0.5 ppm, and said photoreceptor includes a plurality of layers, an uppermost layer being a charge-transferring layer containing a charge-transferring material represented by Formula (1), an oxygen gas permeability coefficient per unit thickness of said charge-transferring layer being not higher than $1.0 \times 10^{-7}$ (cc/cm$^2$.S.cmHg);

wherein said method comprises charging said photoreceptor with said charger to form a charged photoreceptor, exposing said charged photoreceptor to an image to form a latent image, developing said latent image with toner to form a toner image, transferring said toner image to a recording sheet, and cleaning residual toner from said photoreceptor;

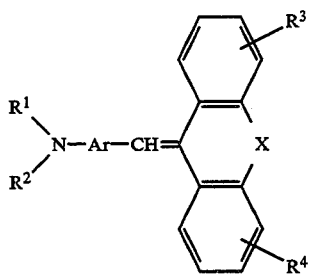

wherein X represents —$CH_2CH_2$ or —CH=CH—, $R^1$ and $R^2$ represent alkyl group, aralkyl group, aromatic ring group, or heterocycle group, $R^3$ and $R^4$ represent a hydrogen atom, alkyl group, alkoxy group, or a halogen atom, and Ar represents aromatic ring group or heterocycle group.

7. The method of claim 6, wherein the charger is a roller type charger.

8. The method of claim 7, wherein the charge-transferring layer contains dimethyl BPZ as a binder.

9. The method of claim 7, wherein the charge-transferring layer contains BPZ as a binder.

* * * * *